United States Patent
Sugiyama

(10) Patent No.: US 9,532,707 B2
(45) Date of Patent: Jan. 3, 2017

(54) LENS FRAME UNIT AND ENDOSCOPE

(71) Applicant: OLYMPUS CORPORATION, Tokyo (JP)

(72) Inventor: Yuta Sugiyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 441 days.

(21) Appl. No.: 14/247,465

(22) Filed: Apr. 8, 2014

(65) Prior Publication Data

US 2014/0221743 A1 Aug. 7, 2014

Related U.S. Application Data

(63) Continuation of application No. PCT/JP2012/076237, filed on Oct. 10, 2012.

(30) Foreign Application Priority Data

Oct. 11, 2011 (JP) .................................. 2011-224158

(51) Int. Cl.
*A61B 1/00* (2006.01)
*A61B 1/06* (2006.01)
(Continued)

(52) U.S. Cl.
CPC ............. *A61B 1/127* (2013.01); *A61B 1/0008* (2013.01); *A61B 1/04* (2013.01); *A61B 1/0676* (2013.01);
(Continued)

(58) Field of Classification Search
None
See application file for complete search history.

(56) References Cited

U.S. PATENT DOCUMENTS 4,916,015 A * 4/1990 Schaffner ............... H01J 35/105
204/157.47
5,386,623 A * 2/1995 Okamoto ............ H01L 21/4846
257/E21.705
(Continued)

FOREIGN PATENT DOCUMENTS

DE 10 2009 013 615 A1 9/2010
JP 2-257926 A 10/1990
(Continued)

OTHER PUBLICATIONS

Extended Supplementary European Search Report dated Sep. 11, 2015 from related European Application No. 12 84 0376.3.
(Continued)

*Primary Examiner* — John P Leubecker
(74) *Attorney, Agent, or Firm* — Scully, Scott, Murphy & Presser, P.C.

(57) ABSTRACT

A lens frame unit includes a lens frame body that houses an optical member, a heat transfer unit that covers at least part of the lens frame body, a heat-generating unit, a temperature measurement unit that measures temperature and a same single electrical wiring board on which the heat-generating unit and the temperature measurement unit are mounted. The heat-generating unit and the temperature measurement unit are arranged on the electrical wiring board so as to be separated from each other, and the electrical wiring board is disposed such that the heat-generating unit and the temperature measurement unit are in contact with the heat transfer unit. Thermal resistance between closest positions of the heat-generating unit and the temperature measurement unit is greater than thermal resistance between the heat-generating unit and the heat transfer unit, and between the temperature measurement unit and the heat transfer unit.

20 Claims, 10 Drawing Sheets

(51) Int. Cl.
*A61B 1/12* (2006.01)
*A61B 1/04* (2006.01)
*G02B 23/24* (2006.01)
*G02B 27/00* (2006.01)

(52) U.S. Cl.
CPC ........... *A61B 1/128* (2013.01); *G02B 23/2492* (2013.01); *G02B 27/0006* (2013.01)

(56) References Cited

U.S. PATENT DOCUMENTS

| | | | |
|---|---|---|---|
| 5,398,689 A * | 3/1995 | Connor | A61B 8/12 600/459 |
| 6,293,910 B1 * | 9/2001 | Yamakita | A61B 1/0011 600/110 |
| 2003/0091089 A1 * | 5/2003 | Krausse | G02B 7/008 374/16 |
| 2007/0149856 A1 * | 6/2007 | Segawa | A61B 1/051 600/169 |
| 2009/0259101 A1 * | 10/2009 | Unsai | A61B 1/00096 600/110 |
| 2010/0016671 A1 * | 1/2010 | Wieters | A61B 1/0008 600/169 |
| 2010/0309553 A1 | 12/2010 | Nagamizu | |
| 2011/0301414 A1 * | 12/2011 | Hotto | A61B 1/00009 600/114 |
| 2012/0034573 A1 | 2/2012 | Erdmann et al. | |
| 2013/0116507 A1 * | 5/2013 | Segawa | A61B 1/00006 600/109 |

FOREIGN PATENT DOCUMENTS

| | | |
|---|---|---|
| JP | 2003-334157 A | 1/2003 |
| JP | 2005-040623 A | 2/2005 |
| JP | 2007-220636 A | 8/2007 |
| JP | 2008-259611 A | 10/2008 |
| JP | 4616421 B2 | 1/2011 |
| WO | 97/31293 A1 | 8/1997 |
| WO | WO 2010/047396 A1 | 4/2010 |
| WO | WO 2010/055753 A1 | 5/2010 |
| WO | WO 2011/010499 A1 | 1/2011 |

OTHER PUBLICATIONS

Chinese Office Action dated Feb. 22, 2016 in related Chinese Application No. 201280050019.6, together with an English language translation.

Partial Supplementary European Search Report dated Jun. 10, 2015 from related European Application No. 12 84 0376.3.

English translation of the International Preliminary Report on Patentability together with the Written Opinion dated Jul. 17, 2014, received in related International Application No. PCT/JP2012/076237.

International Search Report dated Nov. 20, 2012 issued in PCT/JP2012/076237.

Chinese Office Action dated Aug. 5, 2015 from related Chinese Patent Application No. 201280050019.6, together with an English language translation.

* cited by examiner

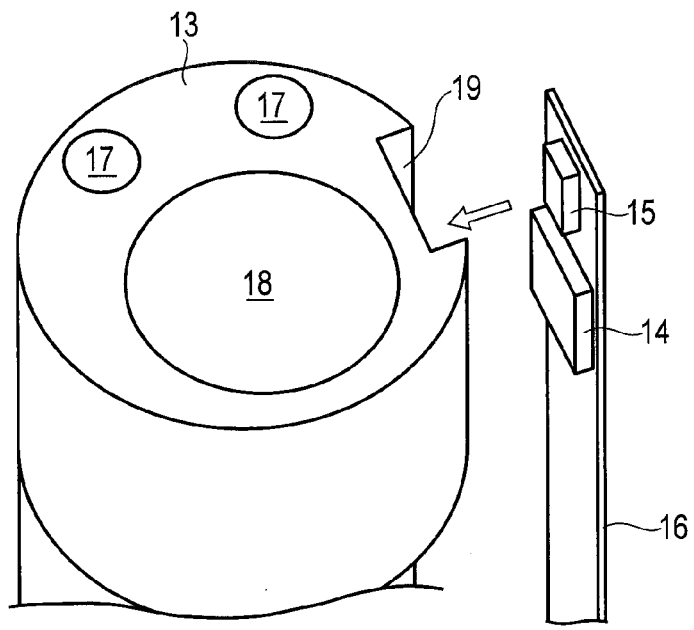
F I G. 4
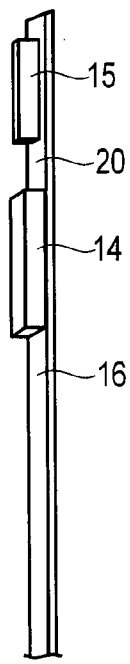
F I G. 5

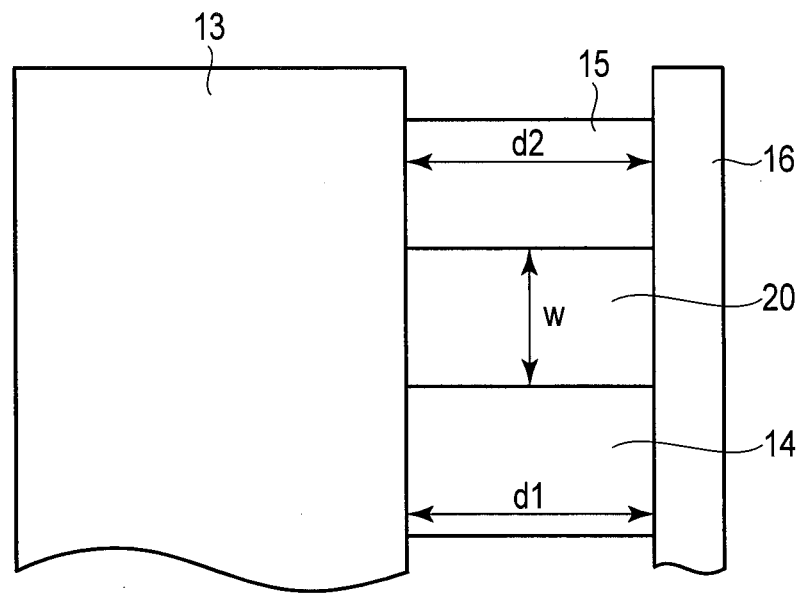
F I G. 7
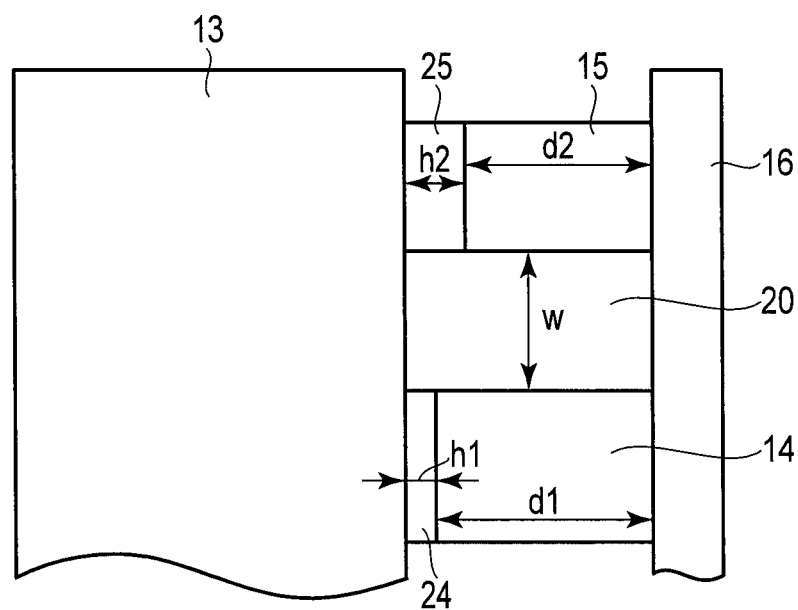
F I G. 8

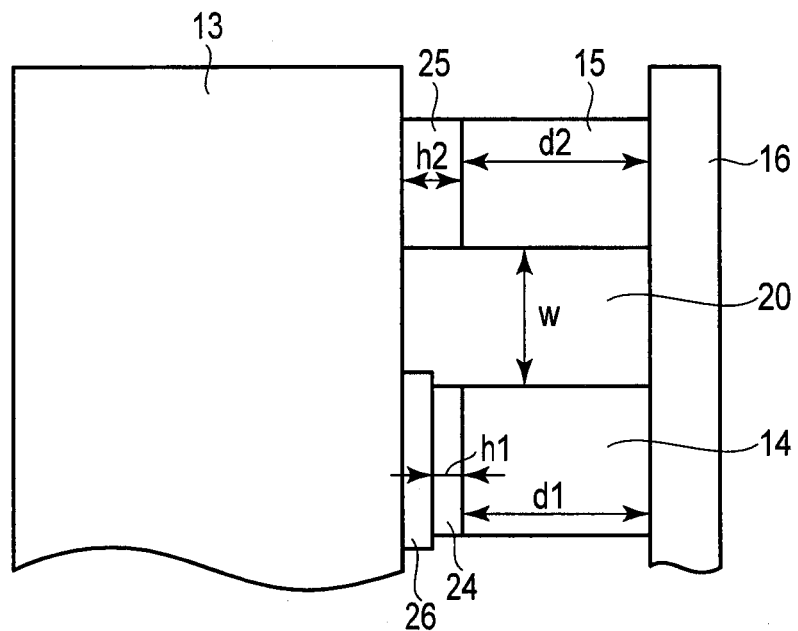
F I G. 9
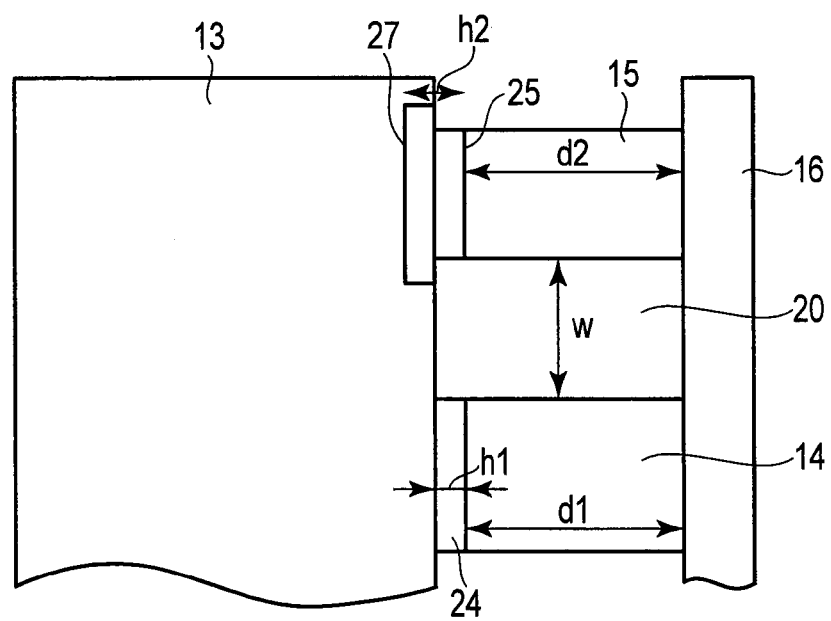
F I G. 10

LENS FRAME UNIT AND ENDOSCOPE

CROSS-REFERENCE TO RELATED APPLICATIONS

This application is a Continuation Application of PCT Application No. PCT/JP2012/076237, filed Oct. 10, 2012 and based upon and claiming the benefit of priority from prior Japanese Patent Application No. 2011-224158, filed Oct. 11, 2011, the entire contents of all of which are incorporated herein by reference.

BACKGROUND OF THE INVENTION

1. Field of the Invention

The present invention relates to a lens frame unit for preventing fogging of an optical member disposed at a distal end and an endoscope including this lens frame unit.

2. Description of the Related Art

Generally, medical endoscopes such as a rigid scope and a flexible scope for being inserted into a body cavity to perform observation or treatment of the inside of the body cavity, and industrial endoscopes for performing inspection or repair in a plant facility are widely used. With such endoscopes, based on an image that is of an object to be observed and is formed on an eyepiece optical system or an imaging unit by an optical member of an objective optical system disposed at a distal end of the endoscope, desired treatment or inspection, for example, is performed.

When an endoscope is inserted into a humid environment such as in a body cavity, if the temperature of the inserted endoscope is lower than the temperature of the environment, fogging due to the temperature difference may occur on an optical member at a distal end of the endoscope, such as on a surface of a lens cover.

To deal with such fogging, for example, Japanese Patent No. 4616421 discloses an endoscope including an anti-fogging unit for preventing fogging of an optical member disposed at a distal end of the endoscope. In this endoscope, behind a lens cover housed in a cylindrical lens frame, a heater formed in a ring shape is arranged. Energizing a heater in advance to heat the lens cover at an appropriate temperature, and then inserting the endoscope into a body cavity, for example, prevent fogging of a surface of the lens cover.

BRIEF SUMMARY OF THE INVENTION

According to one embodiment of the present invention, a lens frame unit includes a lens frame body that houses an optical member, a heat transfer unit that covers at least part of the lens frame body, a heat-generating unit that generates heat, a temperature measurement unit that measures temperature and a same single electrical wiring board on which the heat-generating unit and the temperature measurement unit are mounted, wherein the heat-generating unit and the temperature measurement unit are arranged on the electrical wiring board so as to be separated from each other, and the electrical wiring board is disposed such that the heat-generating unit and the temperature measurement unit are in contact with the heat transfer unit, and thermal resistance between closest positions of the heat-generating unit and the temperature measurement unit is greater than thermal resistance between the heat-generating unit and the heat transfer unit, and thermal resistance between the temperature measurement unit and the heat transfer unit.

According to one embodiment of the present invention, an endoscope including the lens frame unit according to above, the endoscope includes an eyepiece lens with which light passing through the optical member is observed, a terminal unit that performs signal transmission or power supply to the heat-generating unit and signal reception from the temperature measurement unit, a wiring unit that electrically connects the terminal unit and the electrical wiring board and an exterior unit that accommodates the lens frame unit, the eyepiece lens, the terminal unit, and the wiring unit.

According to one embodiment of the present invention, an endoscope including the lens frame unit according to above, the endoscope includes an imaging unit that photoelectrically converts an image formed through the optical member, an image output unit that transmits and outputs a video signal read from the imaging unit, a terminal unit that performs signal transmission or power supply to the heat-generating unit, signal reception from the temperature measurement unit, and video signal reception from the image output unit, a wiring unit that electrically connects the terminal unit and the electrical wiring board and an exterior unit that accommodates the lens frame unit, the imaging unit, the image output unit, the terminal unit, and the wiring unit.

According to the present invention, it is possible to provide a lens frame that can be easily assembled without being limited by space and prevents fogging of an optical member, and an endoscope comprising this lens frame.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a perspective view illustrating a configuration in which a chip heater, a thermistor, and a flexible wiring board are assembled to a heat transfer member of a lens frame unit.

FIG. 5 is a perspective view illustrating the flexible wiring board on which the chip heater and the thermistor are mounted.

FIG. 7 is a diagram illustrating a part of the lens frame unit in a longitudinal section along the line A-A depicted in FIG. 3 in a first embodiment.

FIG. 8 is a diagram illustrating a part of a lens frame unit in a second embodiment, in a section similar to that in FIG. 7.

FIG. 9 is a diagram illustrating a part of a lens frame unit in a modification of the second embodiment, in a section similar to that in FIG. 7.

FIG. 10 is a diagram illustrating a part of a lens frame unit in another modification of the second embodiment, in a section similar to that in FIG. 7.

DETAILED DESCRIPTION OF THE INVENTION

First Embodiment

A first embodiment of the present invention will be described with reference to FIG. 1, FIG. 2, FIG. 3, FIG. 4, FIG. 5, FIG. 6, and FIG. 7.

Figure 1:
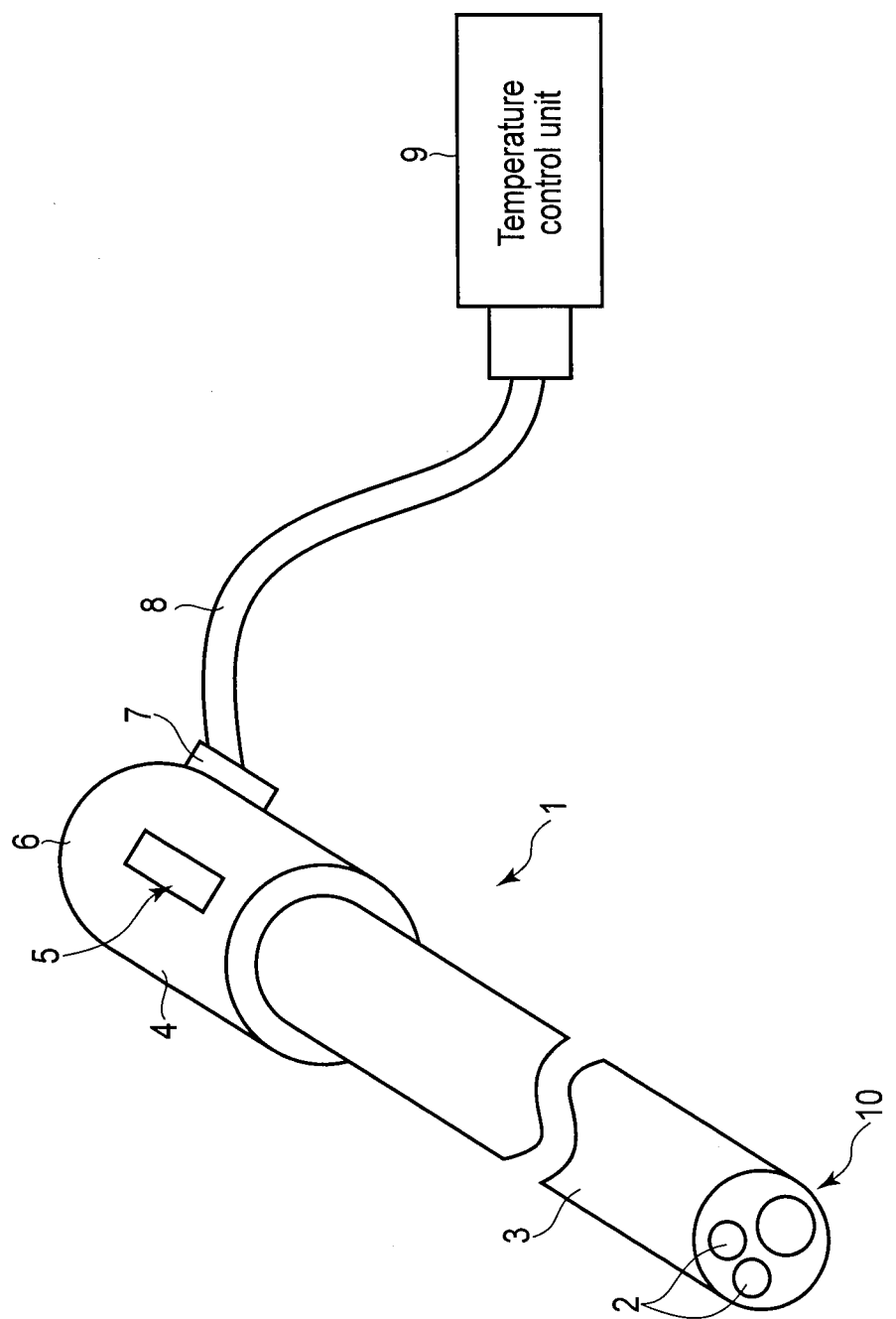
FIG. 1 is a diagram schematically illustrating a configuration of an endoscope (rigid scope).

FIG. 1 is a diagram schematically illustrating a configuration of an endoscope 1 that is a rigid scope. The endoscope 1 comprises a lens frame unit 10 disposed on an endoscope distal side, a light emitting unit 2 for emitting illumination light, a metallic exterior unit 3 covering the whole endoscope body including the lens frame unit 10 and the light emitting unit 2, an operation unit 4 that is disposed on an endoscope proximal side and includes an operation switch 5, an eyepiece lens 6, and a terminal unit 7.

The endoscope 1 is electrically connected to a temperature control unit 9 by an external connection cable 8 connected to the terminal unit 7. The temperature control unit 9 herein is illustrated as a component separate from the endoscope 1, but may be incorporated into the endoscope such as the operation unit 4.

Figure 2:
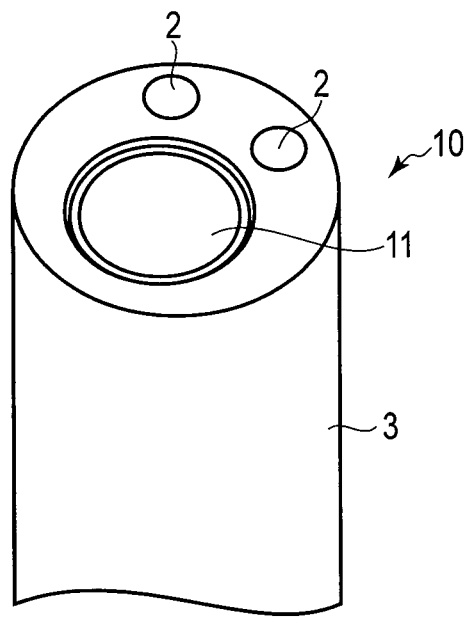
FIG. 2 is a perspective view illustrating an endoscope distal end including a lens frame unit.
Figure 3:
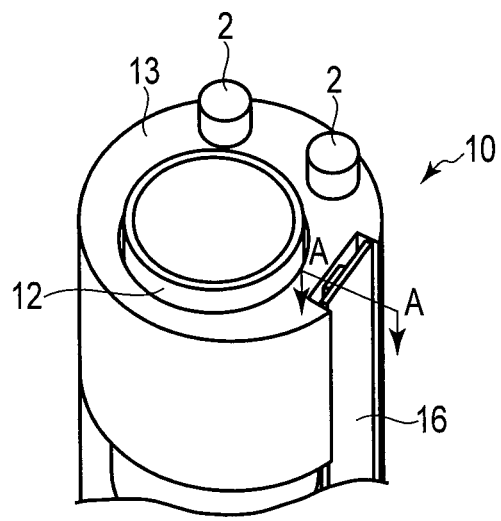
FIG. 3 is a perspective view illustrating the endoscope distal end with an exterior unit removed.

FIG. 2 is a perspective view illustrating an endoscope distal end including the lens frame unit 10 in a state of being covered by the exterior unit 3. FIG. 3 is a perspective view illustrating the endoscope distal end including the lens frame unit 10 with the exterior unit 3 removed. The lens frame unit 10 comprises an objective optical system including an objective lens not depicted and a lens cover 11 covering a surface of the objective lens, a lens frame body 12, a heat transfer member 13, a chip heater 14, a thermistor 15, and a flexible wiring board 16 on which the chip heater 14 and the thermistor 15 are mounted.

The endoscope 1 is configured so that light passing through the lens cover 11 and the objective lens is observed at the eyepiece lens 6. The light emitting unit 2 and the lens cover 11 are exposed at the surface of the endoscope distal end. Alternatively, the endoscope 1 may be configured so that the objective lens is exposed at the surface of the endoscope distal end without the lens cover 11 provided. In the following description, at least one of the lens cover 11 and the objective lens fogging of which is prevented during insertion into a body cavity, for example, is called an optical member.

The lens frame body 12 is a cylindrical member, and houses the objective optical system in the cylinder thereof. The heat transfer member 13 covers almost all of an outer peripheral surface of the lens frame body 12 in FIG. 3, but does not necessarily have to do so, and only has to cover at least part of the outer peripheral surface of the lens frame body 12.

FIG. 4 is a perspective view illustrating a configuration in which the chip heater 14, the thermistor 15, and the flexible wiring board 16 are assembled to the heat transfer member 13 of the lens frame unit 10. The heat transfer member 13 is a heat transfer unit for transferring heat generated by the chip heater 14, and a main material thereof is copper.

In the heat transfer member 13, a first through hole 17 in which the light emitting unit 2 is arranged, a second through hole 18 in which the lens frame body 12 is arranged, and a groove-shaped cutout portion 19 to which the flexible wiring board 16 is attached are formed. The first and second through holes 17 and 18 extend inside the heat transfer member 13 in the longitudinal direction of the endoscope 1. The cutout portion 19 extends on the outer peripheral surface of the heat transfer member 13 in the longitudinal direction of the endoscope 1. The chip heater 14 and the thermistor 15 are brought into contact with and buried into the cutout portion 19 in the direction indicated by the arrow in FIG. 4, thereby being attached to the heat transfer member 13 as depicted in FIG. 3.

FIG. 5 is a perspective view illustrating the flexible wiring board 16 on which the chip heater 14 and the thermistor 15 are mounted. The chip heater 14 is a heat-generating unit for generating heat to prevent fogging of the optical member at the endoscope distal end, and the thermistor 15 is a temperature measurement unit for measuring the temperature at the endoscope distal end. Main material for the chip heater 14 and the thermistor 15 is alumina having a relatively high heat conductivity (about 38 W/m·K at room temperature).

The chip heater 14 and the thermistor 15 are mounted on the same single flexible wiring board 16 in a manner aligned in the longitudinal direction of the lens frame unit 10 (endoscope 1), that is, the chip heater 14 and the thermistor 15 are attached in a line. In the present embodiment, the thermistor 15 is disposed on a further distal side of the endoscope than the chip heater 14. The chip heater 14 and the thermistor 15 are arranged on the flexible wiring board 16 so as to be separated from each other by a predetermined distance, and air within this distance serves as a heat transfer barrier portion 20 for blocking heat transfer between the chip heater 14 and the thermistor 15 under atmosphere.

Figure 6:
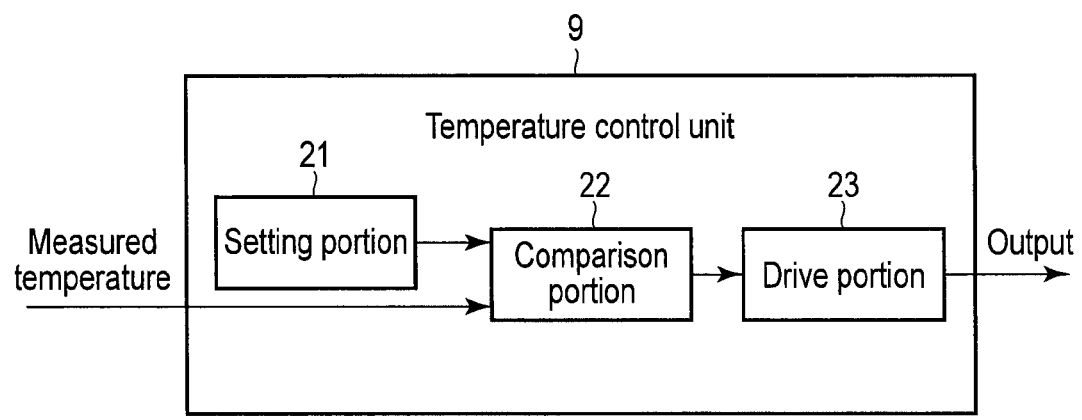
FIG. 6 is a block diagram illustrating a temperature control unit.

FIG. 6 is a block diagram illustrating the temperature control unit 9. The temperature control unit 9 comprises a setting portion 21, a comparison portion 22, and a drive portion 23. In the setting portion 21, a target temperature is set in advance. This target temperature is set to be a temperature making it possible to prevent fogging of the optical member inserted into a body cavity, for example.

When the endoscope 1 is inserted into a body cavity, the temperature at the endoscope distal end measured by the thermistor 15 of the lens frame unit 10 is transmitted to the temperature control unit 9 through a wiring unit such as the flexible wiring board 16 and the external connection cable 8. The temperature control unit 9 compares the target temperature set in the setting portion 21 with the temperature measured by the thermistor 15 (as described later, this measured temperature is close to the temperature of the optical member at the endoscope distal end) in the comparison portion 22. As a result of this comparison, if heating of the endoscope distal end is necessary for anti-fogging of the optical member, a drive signal is output by the drive portion 23 to drive the chip heater 14. The chip heater 14 generates heat so that the temperature measured by the thermistor 15 becomes close to the target temperature to warm up the endoscope distal end. The terminal unit 7 performs signal transmission or power supply to the chip heater 14 and signal reception from the thermistor 15.

As described above, the temperature control unit 9 controls ON/OFF of the chip heater 14 on the basis of the temperature at the endoscope distal end measured by the thermistor 15, thereby functioning to prevent fogging of the optical member.

FIG. 7 is a diagram illustrating a relation of the heat transfer member 13, the chip heater 14, the thermistor 15, the flexible wiring board 16, and the heat transfer barrier portion 20 in a longitudinal section along the line A-A depicted in FIG. 3. It should be noted that each component in FIG. 7 is not necessarily scaled correctly, simply for illustration purposes.

In the present embodiment, as described above, the chip heater 14 and the thermistor 15 are separated from each other by air therebetween. In other words, heat is not easily conducted between the chip heater 14 and the thermistor 15 because of the air as a barrier. This air gap is formed, for example, in a substantially uniform width w=0.5 mm in the longitudinal direction. Here, the radial thickness of the chip heater 14 is denoted by d1, the radial thickness of the thermistor 15 is denoted by d2, and d1=d2=0.2 mm. Also, the heat conductivity of material of the chip heater 14 at room temperature is denoted by $\lambda 1$, the heat conductivity of material of the thermistor 15 is denoted by $\lambda 2$, $\lambda 1 = \lambda 2 = 38$ W/m·K, and the heat conductivity $\lambda 3$ of air is $\lambda 3 = 0.024$ W/m·K.

In this case, an index R1 indicating difficulty of heat transfer between the heat transfer member 13 and the chip heater 14 and an index R2 indicating difficulty of heat transfer between the heat transfer member 13 and the thermistor 15 are expressed as:

$$R1 = R2 = d1/\lambda 1 = d2/\lambda 2 = 0.2/38 \approx 0.0052 \quad \text{Formula (1)}.$$

An index R3 indicating difficulty of heat transfer between the chip heater 14 and the thermistor 15 is expressed as:

$$R3 = w/\lambda 3 = 0.5/0.024 \approx 20.8 \quad \text{Formula (2)}.$$

Thus, the index R3 indicating difficulty of heat transfer between the chip heater 14 and the thermistor 15 is sufficiently larger than the index R1 indicating difficulty of heat transfer between the heat transfer member 13 and the chip heater 14 and also the index R2 indicating difficulty of heat transfer between the heat transfer member 13 and the thermistor 15. In this manner, if the relations of R1<R3 and R2<R3 are satisfied, most of the heat generated by the chip heater 14 flows toward the heat transfer member 13 and almost no heat transfers from the chip heater 14 directly toward the thermistor 15, and thus the heat transfer barrier portion 20 functions satisfactorily as a thermal barrier.

Such indices indicating difficulty of heat transfer are heat transfer properties that can be understood as what are called "thermal resistances". Such thermal resistances are determined based on heat conductivities inherent in materials constituting the heat transfer member 13, the chip heater 14, the thermistor 15, and the heat transfer barrier portion 20, radial thicknesses and longitudinal lengths of these members, distances between these members (distances between positions that are closest to each other among these members), areas of surfaces of these members contacting each other, or shapes of these members, for example.

In the present embodiment, air under atmosphere serves as a heat transfer barrier, but this is not limited to air. Any gas can be similarly used if it is a gas having a heat transfer property similar to that of air such as nitrogen.

Copper that is a main material of the heat transfer member 13 has a high heat conductivity (about 398 W/m·K at room temperature). Because the heat transfer member 13 having such a high heat conductivity is provided to the outer peripheral surface of the lens cover 11 at the endoscope distal end with the lens frame body 12 interposed therebetween, the temperature of the lens cover 11 becomes a temperature close to that of the heat transfer member 13.

The thermistor 15 hardly exchanges heat with the chip heater 14 as described above, and heat is exchanged with the heat transfer member 13 for the most part. Accordingly, the temperature measured by the thermistor 15 can be considered to be the temperature of the heat transfer member 13. In other words, the thermistor 15 can measure a temperature close to the temperature of the lens cover 11. When the heat transfer barrier portion 20 is not appropriately provided, the thermistor 15 may detect the temperature of the chip heater 14 instead of the temperature of the heat transfer member 13, but in the present embodiment, the above-described configuration makes it possible to reliably measure the temperature close to the temperature of the lens cover 11.

In the present embodiment, because the chip heater 14 is attached to the heat transfer member 13 covering at least part of the lens frame body 12, it is possible to provide flexibility in the arrangement of a heater without such a spatial limitation as in the case of providing a heater in the lens frame body 12.

In addition, by providing the heat transfer barrier portion 20 of air having a relatively low heat conductivity, even if the longitudinal width w of the heat transfer barrier portion 20 is shortened, a sufficient difference can be provided between the difficulty of heat transfer, which means the thermal resistance, between the heat transfer member 13 and the chip heater 14 and also between the heat transfer member 13 and the thermistor 15 and the thermal resistance between the chip heater 14 and the thermistor 15. Accordingly, the width w can be narrowed, and thus the lens frame unit 10 and eventually the endoscope 1 can be easily downsized.

In addition, mounting the chip heater 14 and the thermistor 15 on the same single flexible wiring board 16 makes the ease of assembly better than the case of attaching these components separately to the heat transfer member 13, so that assembly becomes easy. The chip heater 14 and the thermistor 15 including the flexible wiring board 16 are also arranged on the outer peripheral surface of the heat transfer member 13 instead of inside the heat transfer member 13. Accordingly, space in which the chip heater 14 and the thermistor 15 including the flexible wiring board 16 are arranged is not limited.

In the present embodiment, the chip heater 14 and the thermistor 15 are disposed and aligned in the longitudinal direction of the endoscope, whereby the width w of the heat transfer barrier portion 20 can be easily obtained.

In addition, the thermistor 15 is disposed on a further distal side of the endoscope than the chip heater 14, whereby the thermistor 15 is located closer to the optical member at the endoscope distal end, so that it is possible to measure the temperature of the optical member more accurately and prevent fogging of the optical member.

The light emitting unit 2 also generates heat when emitting light from the tip thereof. In the present embodiment, the light emitting unit 2, the thermistor 15, and the chip heater 14 are disposed in this order from the endoscope distal side in the longitudinal direction, whereby the thermistor 15 can easily detect heat of both the heat sources of the light emitting unit 2 and the chip heater 14, making it possible to prevent local heat increase.

As described above, in the present embodiment, the configuration to warm the whole endoscope distal end through the heat transfer member arranged on the outer periphery of the lens frame body and thus warm the lens cover makes it possible to improve the flexibility of arrangement of an anti-fogging heater. In addition, mounting the heat-generating unit and the temperature measurement unit on the same electrical wiring board makes it possible to improve the ease of assembly of the lens frame unit. Furthermore, providing the heat transfer barrier between the heat-generating unit and the temperature measurement unit enables the temperature measurement unit to measure the temperature of the heat transfer unit instead of the temperature of the heat-generating unit and eventually measure the temperature of the optical member.

[Modification]

A modification using an insulation adhesive such as an epoxy resin adhesive and a silicone resin adhesive as the heat transfer barrier portion 20 will be described.

The heat conductivity $\lambda 4$ of a typical epoxy resin at room temperature is about 0.25 W/m·K. When other specifications are the same as those in the case of air described above, an index R4 indicating difficulty of heat transfer between the chip heater 14 and the thermistor 15 is expressed as:

$$R4=w/\lambda 4=0.5/0.25\approx 2 \qquad \text{Formula (3)},$$

and such an adhesive functions satisfactorily as the heat transfer barrier portion 20.

Using an adhesive of epoxy resin or silicone resin as the heat transfer barrier portion 20 enables the heat transfer barrier portion 20 to have a function of maintaining a space between the chip heater 14 and the thermistor 15.

The heat conductivity $\lambda 4$ of a general epoxy resin for adhesion or a silicone adhesive is about 0.25 W/m·K, and the maximum values of the thickness d1 of the chip heater 14 and the thickness d2 of the thermistor 15 that can be installed on the endoscope 1 are about d1=d2=0.5 mm. The chip heater 14 and the thermistor 15 are generally constructed of alumina, for example, having a relatively high heat conductivity. Accordingly, if the width w of the heat transfer barrier portion 20 is approximately w=0.1 mm, the following formulae can be obtained:

$$R1=R2=d1/\lambda 1=d2/\lambda 2=0.5/38\approx 0.013 \qquad \text{Formula (4)},$$

and $$R1=w/\lambda 4=0.1/0.25\approx 0.4 \qquad \text{Formula (5)}.$$

Thus, the distance between the closest positions of the chip heater 14 and the thermistor 15 is set equal to or larger than 0.1 mm, whereby the function as the heat transfer barrier portion 20 can be implemented. Alternatively, a filler having similar properties may be used as the heat transfer barrier portion 20.

Second Embodiment

A second embodiment of the present invention will be described with reference to FIG. 8. Similarly to FIG. 7, it should be noted that each component in FIG. 8 and the following drawings is not scaled correctly. The configuration of an endoscope herein in general is the same as that in FIG. 1.

In the first embodiment, a state in which a coupling surface between the heat transfer member 13 and the chip heater 14 and a coupling surface between the heat transfer member 13 and the thermistor 15 are ideal is described. In the second embodiment, a lens frame unit 10 comprises a chip heater coupling layer 24 for coupling a chip heater 14 to a heat transfer member 13 and a thermistor coupling layer 25 for coupling a thermistor 15 to the heat transfer member 13.

FIG. 8 is a diagram illustrating a relation of the heat transfer member 13, the chip heater 14, the thermistor 15, a flexible wiring board 16, a heat transfer barrier portion 20, the chip heater coupling layer 24, and the thermistor coupling layer 25 in the second embodiment, in a section along the line A-A depicted in FIG. 3. In the present embodiment, the material of each of the heat transfer barrier portion 20, the chip heater coupling layer 24, and the thermistor coupling layer 25 is an epoxy resin adhesive.

Here, the heat conductivity $\lambda 5$ of the chip heater coupling layer 24 and the heat conductivity $\lambda 6$ of the thermistor coupling layer 25 are $\lambda 5=\lambda 6=0.25$ W/m·K similarly to the above-described modification. Also, the radial thickness d1 of the chip heater 14 and the radial thickness d2 of the thermistor 15 are d1=0.2 mm and d2=0.18 mm, and the radial height h1 of the chip heater coupling layer 24 and the radial height h2 of the thermistor coupling layer 25 are h1=0.01 mm and h2=0.03 mm. Other specifications are the same as those in the first embodiment.

In this case, an index R5 indicating difficulty of heat transfer between the heat transfer member 13 and the chip heater 14 considering the chip heater coupling layer 24 is expressed as:

$$R5=d1/\lambda 1+h1/\lambda 5=0.2/38+0.01/0.25\approx 0.0045 \qquad \text{Formula (6)},$$

and an index R6 indicating difficulty of heat transfer between the heat transfer member 13 and the thermistor 15 considering the thermistor coupling layer 25 is expressed as:

$$R6=d2/\lambda 2+h2/\lambda 6=0.18/38+0.03/0.25\approx 0.12 \qquad \text{Formula (7)}.$$

An index R3 indicating difficulty of heat transfer between the chip heater 14 and the thermistor 15 is evaluated similarly to Formula (2).

Thus, the index R3 indicating difficulty of heat transfer between the chip heater 14 and the thermistor 15 is sufficiently larger than the index R5 indicating difficulty of heat transfer between the heat transfer member 13 and the chip heater 14 including the chip heater coupling layer 24 and also the index R6 indicating difficulty of heat transfer between the heat transfer member 13 and the thermistor 15 including the thermistor coupling layer 25. In this manner, if the relations of R5<R3 and R6<R3 are satisfied, the heat transfer barrier portion 20 functions satisfactorily as a thermal barrier.

In the present embodiment, by using an adhesive such as an epoxy resin, fixation of the chip heater 14 and the thermistor 15 onto the heat transfer member 13 and filling of the epoxy resin into the heat transfer barrier portion 20 can be performed simultaneously, whereby the ease of assembly is improved.

In the present embodiment, the chip heater 14 is thicker than the thermistor 15. Accordingly, when the chip heater 14 and the thermistor 15 are pressed and bonded onto a cutout portion 19 of the heat transfer member 13 from the side of flexible wiring board 16, the height h1 of the chip heater coupling layer 24 can be made thinner than the height h2 of the thermistor coupling layer 25, and the following formula holds:

$$h1/\lambda 5=0.04<0.12=h2/\lambda 6 \qquad \text{Formula (8)}.$$

Thus, heat-transfer properties between the heat transfer member 13 and the chip heater 14 in which the amount of heat transferring is largest can be improved.

Alternatively, with air used as the heat transfer barrier portion 20, the chip heater 14 and the thermistor 15 may be brazed or soldered to the heat transfer member 13. Brazing alloy or solder containing metal has a heat conductivity higher than that of an adhesive of epoxy resin or silicone resin. Accordingly, the difference in the heat-transfer properties from the heat transfer barrier portion 20 can be made larger. In addition, drying time or heat insulation time is not necessary, and thus the processing time can be made shorter than that of the method using an adhesive.

[Modification]

In a modification depicted in FIG. 9, a portion (cutout portion 19) of the heat transfer member 13 that is in contact with the chip heater 14 is provided with a heat transfer member projecting portion 26 that protrudes from a surface of the cutout portion 19 to the outside in the radial direction. This enables the chip heater coupling layer 24 to be made thinner.

In contrast, in a modification depicted in FIG. 10, a portion (cutout portion 19) of the heat transfer member 13 that is in contact with the thermistor 15 is provided with a heat transfer member recess portion 27 that is recessed from the surface of the cutout portion 19 to the inside in the radial direction. The heat transfer member recess portion 27 is filled with the thermistor coupling layer 25 that is an epoxy resin, for example. Such a configuration also enables the chip heater coupling layer 24 to be made thinner.

Third Embodiment

A third embodiment of the present invention will be described with reference to FIG. 11. The configuration of an endoscope herein in general is the same as that in FIG. 1.

Figure 11:
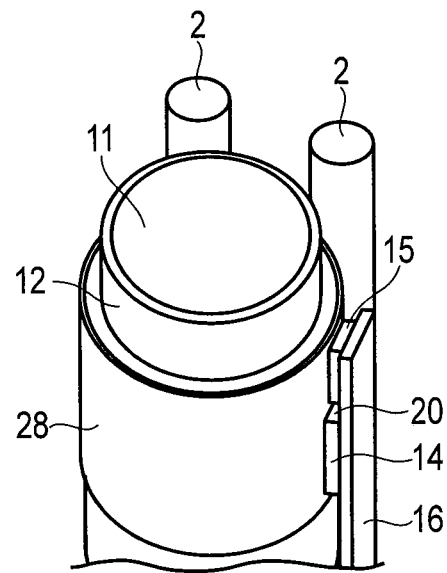
FIG. 11 is a perspective view illustrating an endoscope distal end including a lens frame unit of a third embodiment.

FIG. 11 is a perspective view illustrating an endoscope distal end including a lens frame unit of the third embodiment. In the third embodiment, a heat transfer member 28 containing a graphite sheet is used instead of the heat transfer member 13 containing copper. A main material of the graphite sheet is carbon, which has a very high heat conductivity of 800 W/m·K in a surface direction (lateral direction). The uniformity of heat transfer that is thermal uniformity is also high.

In the present embodiment, the heat transfer member 28 containing a graphite sheet having a thickness of 0.1 mm is wound around at least part of an outer peripheral surface of a lens frame body 12. A chip heater 14 and a thermistor 15 are disposed in intimate contact with the heat transfer member 28. Between the chip heater 14 and the thermistor 15, a heat transfer barrier portion 20 of air or a resin is provided similarly to the first and second embodiments.

Also in the present embodiment, most of the heat generated by the chip heater 14 transfers to the heat transfer member 28. Because this heat transfer member 28 warms a lens frame body 12 and a lens cover 11 housed therein, the temperature of the lens cover 11 at the endoscope distal end becomes almost the same as that of the heat transfer member 28 containing a graphite sheet. In addition, providing the heat transfer barrier portion 20 enables the thermistor 15 to measure the temperature of the heat transfer member 28 instead of the temperature of the chip heater 14. Thus, the temperature of the lens cover 11 can be measured.

In the present embodiment, because the heat conductivity of the heat transfer member 28 is very high, satisfactory heat-transfer properties are obtained even if the heat transfer member 28 wound around the outer peripheral surface of the lens frame body 12 is small. Thus, it is possible to reliably warm the optical member to prevent fogging thereof.

In addition, the proximal end of the heat transfer member 28 wound around the outer peripheral surface of the lens frame body 12 is extended to the proximal side by about several to several tens millimeters, whereby the chip heater 14 and the thermistor 15 are brought into contact with this extended proximal end portion. As described above, in the present embodiment, even without disposing the chip heater 14 and the thermistor 15 on the endoscope distal side where space is more likely to be insufficient because members are densely packed therein, it is possible to warm the optical member from the chip heater 14 through the heat transfer member 28 or measure the temperature of the heat transfer member 28 and eventually the temperature of the optical member with the thermistor 15.

As a sheet-shaped member that mainly contains carbon, not only the graphite sheet, but also a material such as carbon nanotubes that is excellent in heat transfer properties can be employed as appropriate.

Fourth Embodiment

A fourth embodiment of the present invention will be described with reference to the FIG. 12. The configuration of an endoscope herein in general is the same as that in FIG. 1.

Figure 12:
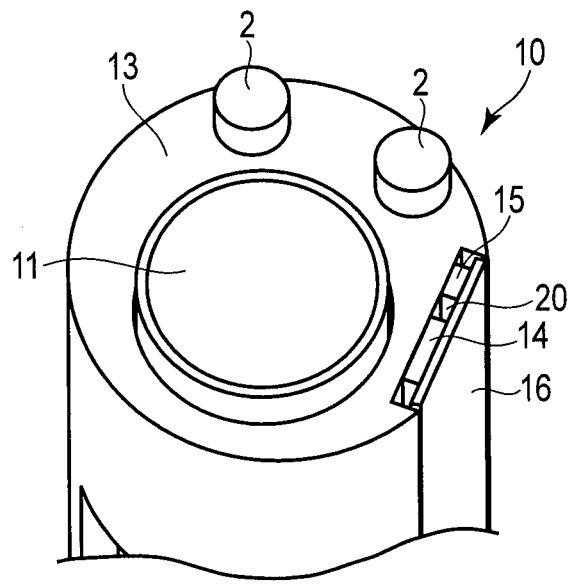
FIG. 12 is a perspective view illustrating an endoscope distal end including a lens frame unit of a fourth embodiment.

FIG. 12 is a perspective view illustrating an endoscope distal end including a lens frame unit of the fourth embodiment. In the present embodiment, a chip heater 14 and a thermistor 15 are disposed at an endoscope distal end and in the circumferential direction of a lens frame unit 10, in other words, aligned in the radial direction. The thermistor 15 is disposed on the side closer to a light emitting unit 2 than the chip heater 14 is. Between the chip heater 14 and the thermistor 15, a heat transfer barrier portion 20 of air or a resin is provided.

By aligning and disposing the chip heater 14 and the thermistor 15 in the radial direction, both the chip heater 14 and the thermistor 15 can be disposed near a lens cover 11. This improves ease of heating an optical member by the chip heater 14 and also accuracy of temperature detection by the thermistor 15.

Furthermore, by disposing the thermistor 15 between the light emitting unit 2 and the chip heater 14 in the radial direction, heat of both the heat sources of the light emitting unit 2 and the chip heater 14 can be easily detected by the thermistor 15, and thus local temperature increase can be prevented.

Fifth Embodiment

A fifth embodiment of the present invention will be described with reference to FIG. 13, FIG. 14, and FIG. 15. Hereinafter, a main configuration and characterizing portions of the fifth embodiment will be described, and description of a configuration that is the same as that in the first embodiment is omitted.

Figure 13:
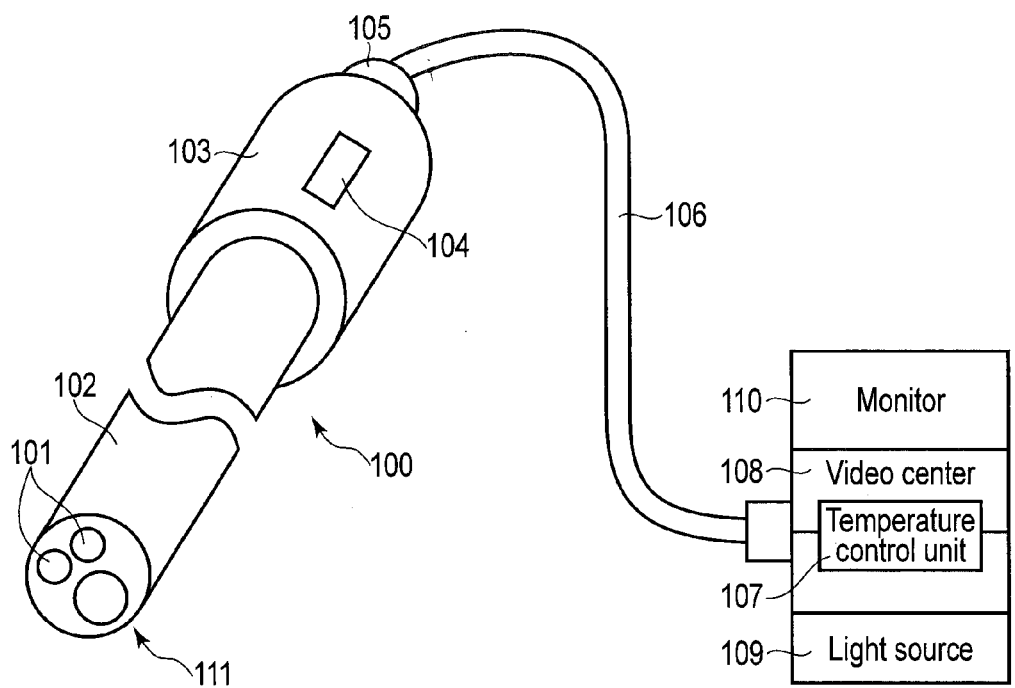
FIG. 13 is a diagram schematically illustrating a configuration of an endoscope (electronic endoscope).

FIG. 13 is a diagram schematically illustrating a configuration of an endoscope 100 that is an electronic endoscope. The endoscope 100 comprises a lens frame unit 111 disposed on an endoscope distal side, a light emitting unit 101 for emitting illumination light, a metallic exterior unit 102 covering the whole endoscope body including the lens frame unit 111 and the light emitting unit 101, an operation unit 103 that is disposed on an endoscope proximal side and includes an operation switch 104, and a terminal unit 105.

The endoscope 100 is electrically connected to a temperature control unit 107, a video center 108, a light source 109, and a monitor 110 by an external connection cable 106 connected to the terminal unit 105. The external connection cable 106 is a universal cord for transmitting and receiving signals to and from the temperature control unit 107, transmitting video signals to the video center 108, and guiding illumination light to the light emitting unit 101.

Figure 14:
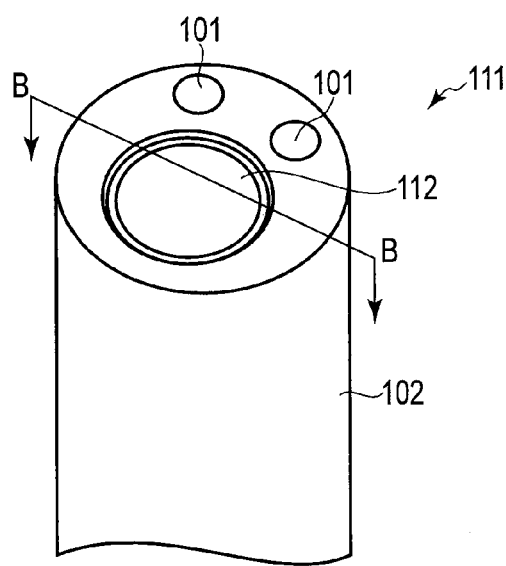
FIG. 14 is a perspective view illustrating an endoscope distal end including a lens frame unit.
Figure 15:
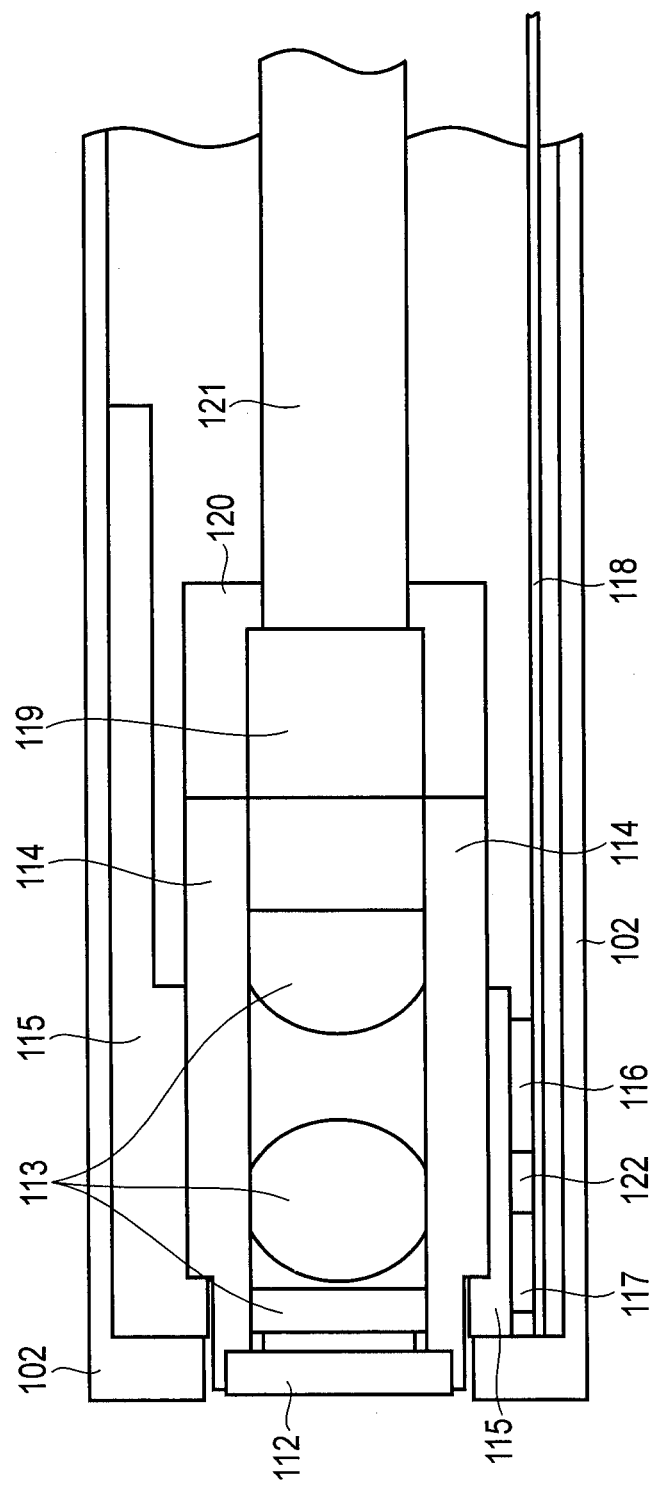
FIG. 15 is a longitudinal sectional view illustrating an internal configuration of an endoscope in a fifth embodiment, in a longitudinal section along the line B-B depicted in FIG. 14.

FIG. 14 is a perspective view illustrating an endoscope distal end including the lens frame unit 111 in a state covered by the exterior unit 102. FIG. 15 is a longitudinal sectional view illustrating an internal configuration of the endoscope 100 in a longitudinal section along the line B-B depicted in FIG. 14. The lens frame unit 111 comprises an objective optical system including an objective lens 113 and a lens cover 112 covering a surface thereof, a lens frame body 114, a heat transfer member 115, a chip heater 116, a thermistor 117, and a flexible wiring board 118 on which the chip heater 116 and the thermistor 117 are mounted. In the present embodiment, the flexible wiring board 118 extends to the terminal unit 105.

On the endoscope proximal side of the lens frame body 114, an imaging unit 119 fixed on an imaging unit fixing frame 120 and an image output cable 121 that is an image output unit connected to the imaging unit 119 are disposed. The image output cable 121 is connected to the terminal unit 105.

When performing observation, for example, with the endoscope 100, the imaging unit 119 photoelectrically converts an image formed through the objective optical system. A video signal read from imaging unit 119 is transmitted and output to the terminal unit 105 through the image output cable 121. The terminal unit 105 performs signal transmission or power supply to the chip heater 116, signal reception from the thermistor 117, and video signal reception from the image output cable 121.

The chip heater 116 and the thermistor 117 are separated by a predetermined distance therebetween, which forms a heat transfer barrier portion 122. In the present embodiment, the heat transfer barrier portion 122 contains a resin having a relatively low heat conductivity.

Also in the present embodiment, similarly to the above-described embodiments, the arrangement of a heater is flexible, making it possible to provide an endoscope excellent in ease of assembly.

Sixth Embodiment

A sixth embodiment of the present invention will be described with reference to FIG. 16. In the sixth embodiment, because a configuration of an endoscope herein is the same as that of the endoscope 100 in the fifth embodiment, description thereof is omitted. Hereinafter, a configuration different from that of the endoscope 100 will be described.

Figure 16:
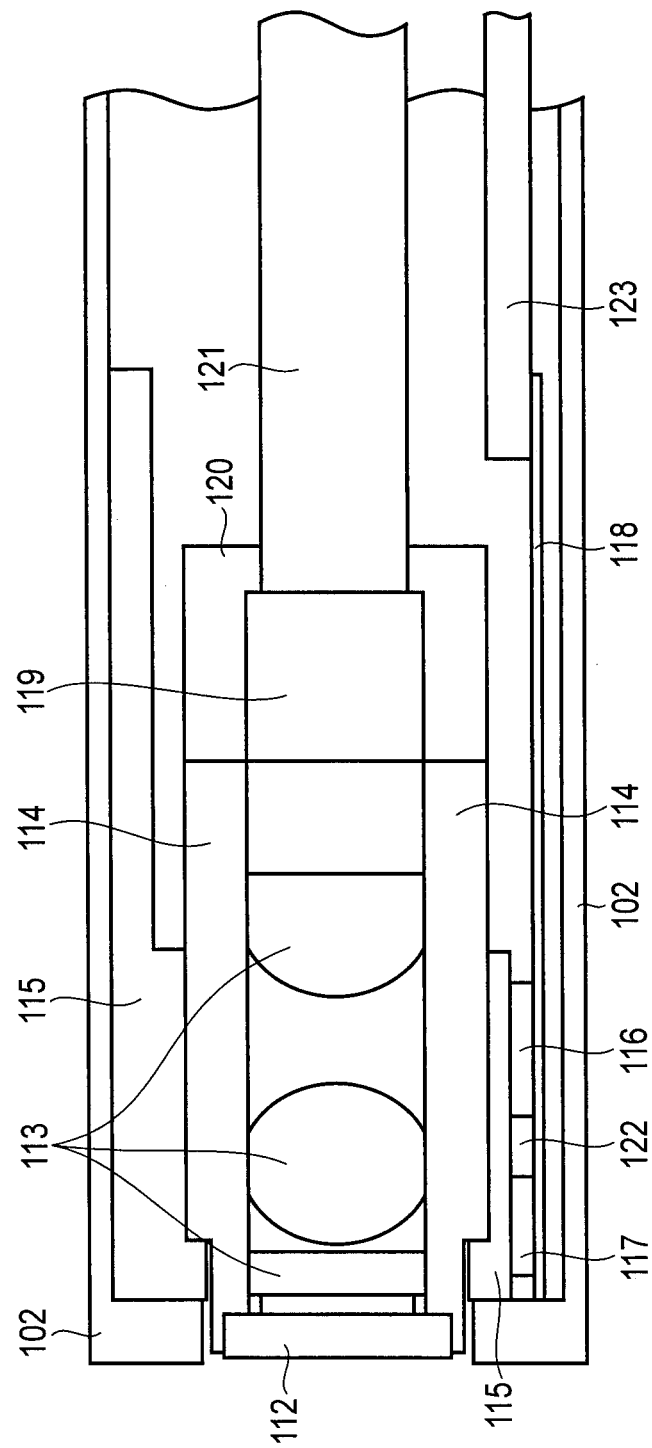
FIG. 16 is a longitudinal sectional view illustrating an internal configuration of an endoscope in a sixth embodiment, in a section similar to that in FIG. 15.

FIG. 16 is a longitudinal sectional view illustrating an internal configuration of the endoscope in the longitudinal section along the line B-B depicted in FIG. 14. In this endoscope, a flexible wiring board 118 on which a chip heater 116 and a thermistor 117 are mounted is replaced with an electric wire 123 in the middle thereof, and this electric wire 123 extends to a terminal unit 105.

Heat generated from a light emitting unit 101 and an imaging unit 119 is conducted to a heat transfer member 115, whereby the temperature is made uniform. When the temperature of the heat transfer member 115 approaches a target temperature by a heat of the light emitting unit 101 and the imaging unit 119, heat given by the chip heater 116 decreases.

Also in the endoscopes 100 of the fifth and sixth embodiments, such a lens frame unit as described in the modification of the first embodiment, the second embodiment and the modification thereof, and the third and fourth embodiments may be employed as appropriate.

Alternatively, as modifications of the first to sixth embodiments, the following modes can be adopted.

As a temperature measurement unit, not only a thermistor, but also a platinum temperature sensor or a thermocouple may be used. As a heat-generating unit, not only a chip heater, but also other resistance heating, or heat generation by a LED, magnetic loss, or dielectric loss may be utilized.

As an electrical wiring board, not only a flexible wiring board, but also a rigid wiring board may be used.

As a heat transfer member, not only copper or a graphite sheet, a material such as aluminum having a high heat conductivity may be used.

Although the respective embodiments and the modifications thereof of the present invention have been described above, the present invention is not limited to these, and various alterations and modifications can be made within a range not departing from the gist of the present invention.

What is claimed is:

1. A lens frame apparatus comprising:
a lens frame body that houses an optical member;
a heat transfer material that covers at least part of the lens frame body;
a chip heater that generates heat;
a temperature measurement sensor that measures temperature; and
an electrical wiring board on which the chip heater and the temperature measurement sensor are mounted, wherein
the chip heater and the temperature measurement sensor are arranged on the electrical wiring board so as to be separated from each other, and the electrical wiring board is disposed such that the chip heater and the temperature measurement sensor are in contact with the heat transfer material, and
thermal resistance between closest positions of the chip heater and the temperature measurement sensor is greater than thermal resistance between the chip heater and the heat transfer material, and thermal resistance between the temperature measurement sensor and the heat transfer material;
wherein
relations of $d1/\lambda1 < w/\lambda3$ and $d2/\lambda2 < w/\lambda3$ are satisfied where a thickness of the chip heater is denoted by d1, a heat conductivity of material of the chip heater is denoted by $\lambda1$, a thickness of the temperature measurement sensor is denoted by d2, a heat conductivity of material of the temperature measurement sensor is denoted by $\lambda2$, a distance between the closest positions of the chip heater and the temperature measurement sensor is denoted by w, and a heat conductivity between the chip heater and the temperature measurement sensor is denoted by $\lambda3$; and
when the chip heater and the heat transfer material are coupled by a first coupling layer therebetween and the temperature measurement sensor and the heat transfer material are coupled by a second coupling layer therebetween, relations of $d1/\lambda1 + h1/\lambda5 < w/\lambda3$ and $d2/\lambda2 + h2/\lambda6 < w/\lambda3$ are satisfied where a thickness of the first coupling layer is denoted by h1, a heat conductivity of the first coupling layer is denoted by $\lambda5$, a thickness of the second coupling layer is denoted by h2, and a heat conductivity of the second coupling layer is denoted by λ6.

2. The lens frame apparatus according to claim 1, wherein a relation of h1/λ5<h2/λ6 is satisfied.

3. The lens frame apparatus according to claim 1, wherein the chip heater and the temperature measurement sensor are separated from each other by a gas.

4. The lens frame apparatus according to claim 1, wherein the chip heater and the temperature measurement sensor are separated from each other with an insulating material interposed therebetween.

5. The lens frame apparatus according to claim 4, wherein the insulating material is an epoxy resin adhesive or a silicone resin adhesive.

6. The lens frame apparatus according to claim 4, wherein the insulating material is a filler.

7. The lens frame apparatus according to claim 1, wherein the heat transfer material mainly contains copper and covers at least part of an outer circumference of the lens frame body.

8. The lens frame apparatus according to claim 1, wherein the heat transfer material is a sheet mainly containing carbon and covers at least part of an outer circumference of the lens frame body.

9. The lens frame apparatus according to claim 1, wherein the chip heater and the temperature measurement sensor are disposed and aligned in a longitudinal direction of the lens frame apparatus.

10. The lens frame apparatus according to claim 9, wherein the temperature measurement sensor is disposed on a further distal side of the lens frame apparatus than the chip heater.

11. The lens frame apparatus according to claim 1, wherein the chip heater and the temperature measurement sensor are disposed on a distal side of the lens frame apparatus, aligned in a circumferential direction of the lens frame apparatus.

12. The lens frame apparatus according to claim 11, further comprising a light source disposed at a distal end of the lens frame apparatus, wherein the temperature measurement sensor is disposed on a side closer to the light source than the chip heater is.

13. The lens frame apparatus according to claim 1, wherein the distance between the closest positions of the chip heater and the temperature measurement sensor is thicker than the thickness of the first coupling layer and the thickness of the second coupling layer.

14. The lens frame apparatus according to claim 1, wherein the chip heater and the heat transfer material are coupled so that amount of heat transferred therebetween is largest among amounts of heats transferred between other members.

15. The lens frame apparatus according to claim 1, wherein the thickness of the first coupling layer is thinner than the thickness of the second coupling layer.

16. The lens frame apparatus according to claim 15, wherein the thickness of the chip heater is thicker than the thickness of the temperature measurement sensor.

17. The lens frame apparatus according to claim 16, wherein a portion of the heat transfer material that is in contact with the chip heater is in a projected shape, or a portion of the heat transfer material that is in contact with the temperature measurement sensor is in a recessed shape.

18. An endoscope including the lens frame apparatus according to claim 1, the endoscope comprising:
an eyepiece lens with which light passing through the optical member is observed;
a terminal that performs signal transmission or power supply to the chip heater and signal reception from the temperature measurement sensor;
wiring that electrically connects the terminal and the electrical wiring board; and
an exterior casing that accommodates the lens frame apparatus, the eyepiece lens, the terminal, and the wiring.

19. An endoscope including the lens frame apparatus according to claim 1, the endoscope comprising:
an imaging sensor that photoelectrically converts an image formed through the optical member;
an image output cable that transmits and outputs a video signal read from the imaging sensor;
a terminal that performs signal transmission or power supply to the chip heater, signal reception from the temperature measurement sensor, and video signal reception from the image output cable;
wiring that electrically connects the terminal and the electrical wiring board; and
an exterior casing that accommodates the lens frame apparatus, the imaging sensor, the image output cable, the terminal, and the wiring.

20. The endoscope according to claim 19, further comprising a controller that is connected to the terminal, wherein the controller is configured to:
set a target temperature;
compare a measured temperature measured by the temperature measurement sensor with the target temperature; and
drive the chip heater based on the comparison so that the measured temperature approaches the target temperature.

* * * * *